(12) United States Patent
Mesaeli

(10) Patent No.: US 7,323,617 B2
(45) Date of Patent: Jan. 29, 2008

(54) TIE-2 DRIVEN OVEREXPRESSION OF CALRETICULIN AS AN INDUCER OF NON-SMALL CELL CARCINOMA OF LUNG

(76) Inventor: Nasrin Mesaeli, 631 Drake Centre, Winnipeg, Manitoba (CA) R3T 5V4

( * ) Notice: Subject to any disclaimer, the term of this patent is extended or adjusted under 35 U.S.C. 154(b) by 0 days.

(21) Appl. No.: 11/671,058

(22) Filed: Feb. 5, 2007

(65) Prior Publication Data

US 2007/0234435 A1    Oct. 4, 2007

Related U.S. Application Data

(60) Provisional application No. 60/790,790, filed on Apr. 11, 2006, provisional application No. 60/764,751, filed on Feb. 3, 2006.

(51) Int. Cl.
*C12N 15/00*  (2006.01)
*G01N 33/00*  (2006.01)
*A01K 67/027* (2006.01)

(52) U.S. Cl. .................... 800/18; 800/3; 435/320.1
(58) Field of Classification Search ............... 800/18, 800/3; 435/320.1
See application file for complete search history.

(56) References Cited

U.S. PATENT DOCUMENTS 7,186,882 B2 *    3/2007    Mesaeli ................. 800/18

OTHER PUBLICATIONS

Schlaeger (PNAS, 1997, vol. 94, No. 7, p. 3058-3063).*
Minami (Arteroscleросis, Thrombosis, and Vascular Biology, 2003, vol. 23, p. 2041-2047).*

* cited by examiner

*Primary Examiner*—Michael C. Wilson
(74) *Attorney, Agent, or Firm*—Michael R. Williams; Ryan W. Dupuis; Adrian D. Battison

(57) ABSTRACT

A transgenic mouse whose genome comprises a Tie-2 promoter operably linked to a cDNA encoding calreticulin (CRT) is described.

3 Claims, 13 Drawing Sheets

```
   1  agtggatgag gtttagtgtt aggcattcag gaaatagagt aaaaggaaat
  51  gaattatggt catcaggtgc taggtgtgtg tgtgtgtgtg tgtgtgtgtg
 101  tgtgtgtgtg tgtgtgtgta tgactgacat cacctataag acctgtaagt
 151  attttatggt atttagtctt tatcgggcaa aggacttacc agcaccactg
 201  taaagatgat gtaaatgagc ccagagggag atgaagtgtt ccttagaca
 251  tcatctcgct aatctcgata agaacttaat gtggaaccat agtaatattt
 301  ttctgaaaat atctcctgct tttgaagaga ctggacttt gccagactac
 351  aactaagttt gtaatatact ctgaggttac ttaagtctat gtattcaatc
 401  tgctgtccta ccgtgtactg tgccttctaa ctggtttaac ctgcctttaa
 451  gaaagcaatg taagtgaccc ttaccctgcc ttggatttcc catgcaatca
 501  gcttttatac cctaaggcaa tgcatagttt taatcttaac taggtactct
 551  ccacacccct gaccatgaat aatctacata tgtgtgtata ctgtggtaat
 601  aatatgctga aagcagccat caggttgaga acaaccttaa acaacaaaca
 651  ctgtaacagt tcaaagcaac atggatgtag gttgattaca tcttcacgtg
 701  gttttaggtg ctattctgga gtactaaagt tcccctgtg tacaactctt
 751  aaaattcact gtctagacgt atcccgcgtg ccttcccta ccatgctttc
 801  tgtgctgttc aataaatacg gagcagagcc cttgttaca acagggaaca
 851  tagacagaca gctaggacag acacaagtaa aacatgtata acagcccggt
 901  aatacagaca gacctcaggc caagtttcac acagattttt cctagggaga
 951  gggatggcct tgctcttggt ctaaactact ccaagaggaa gtctcttttg
1001  tcaccatttt tgtgacactg acacattttg tcgcccctc cacccccc
1051  cccccgctc ttctgagttt ttttaaataa tatttgaaa atgaaggtct
1101  ataaagttag cataagtgga tatagttgtt gatacagacc tttagtgtgc
1151  ttagtgggca gtattctaaa atcaattcac taattaaaaa ctaataatga
1201  taatttatta ataatattat actatcttca tttcttagct taattgagca
1251  agcatttaat taatgcctaa ctatgcctca atcaatatag tagagcatat
1301  attgtacata catacttgta cacacacaca cacacacaca cacacacaca
1351  cacacacaca cacattatgt tcaagtctat tgcagatcag gtatgcagtg
1401  gggaagtgga agaagtaagg tctagcagat gaaaggactt gattccttgg
1451  taaagaattt tgattctgtc cagtgggata caggcacatg atcagaacat
1501  tttaaaatga ttgttcatat aactattttt tattaattaa ttatttatt
1551  tatttatatc cctaatgtta ccctctccag gtccccctt gcagagttct
1601  tctccccatc ccctttcct tcacctctga gagggtaccc ccccccaag
1651  gggggcatca agtctctaca ggattaggtg tatcccattg aggccagaca
1701  aagaagttgt ctgctacatg tgcaaggggc ccttggacca gccatgtat
1751  gctctggtgg cttagtctct gagcgctcgc aggggtctgg gttaattgag
1801  actgtggtct ccctatgggg ttggcatccc catcagtttc ttcagtcctt
1851  ctcctattct tccatagagg tctctgactt cggtccaatg cttgactgta
1901  agtatctgca tctgtctcag tcagctgctg gtagagcctc tcagaggaca
1951  gccatgttag gctcctgact gcaagcacaa catgacatca gtaatagtgt
2001  tacggattgg tgcctgccca taggacatat cccttgcaga ccctaagaga
2051  tccaatgact gtttttaaat gaggctttag gcaagaggag ctttacttga
```

Figure 2 (SEQ ID NO: 3)

```
  1 ccatggggac atggctgtca tggtgtggaa gtgatagaaa tgaaaacatg
 51 tatggatctg tcacaggagc tggtgaggct gatgggtgtg tgggtggcca
101 ctgtttgctc tctgcttgtc acagcctctt gttcagggct tgatcaggga
151 ggtgtgtgtg tgtgtgtgtg tgtgtgtgtg tgtgtgtgtg tgtggtcaca
201 cccatctcag cagatctgtc agcttcccg ctttgttag agggtgatat
251 catgcttcct gggggagct ctggaagaca atgagcagcc actttcctct
301 aga
```

Figure 3 (SEQ ID NO: 4)

E. *wt*   F. *congestion*   G. *adenoma*   H. *adenocarcinoma*

A
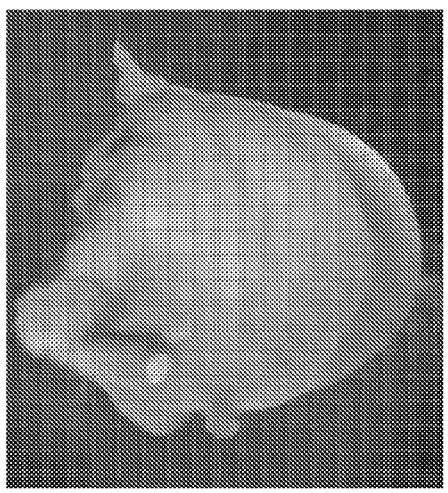
B
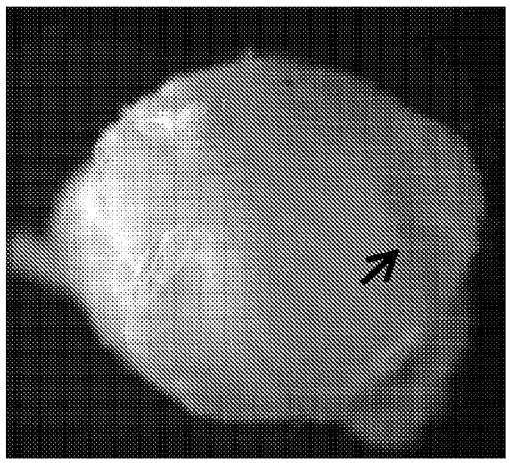
C
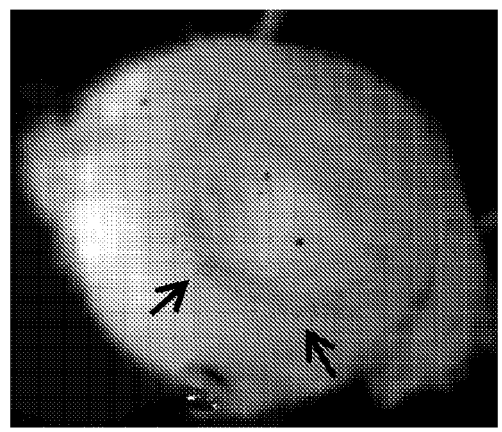
Figure 13

US 7,323,617 B2

TIE-2 DRIVEN OVEREXPRESSION OF CALRETICULIN AS AN INDUCER OF NON-SMALL CELL CARCINOMA OF LUNG

PRIOR APPLICATION INFORMATION

This application claims the benefit of U.S. Provisional Patent Application 60/764,751, filed Feb. 3, 2006 and U.S. Provisional Patent Application 60/790,790, filed Apr. 11, 2006.

FIELD OF THE INVENTION

The present invention relates generally to the field of animal models for human diseases. More specifically, it relates to a transgenic mouse usable as an animal model for non-small cell carcinoma of lung which metastasises to other organs.

BACKGROUND OF THE INVENTION

Transgenic mice technology involves the introduction of new or altered genetic material into the mouse germ line. This results in lineages that carry the new integrated genetic material.

Endoplasmic reticulum (ER) plays an important role in many functions of the cell. ER is not only the protein folding and processing machinery of the cell but it plays an important role in $Ca^{2+}$ storage and regulation of intracellular $Ca^{2+}$ homeostasis (Pozzan, Rizzuto et al. 1994). It is also important in gene regulation (unfolded protein response) (Welihinda, Tirasophon et al. 1997; Tirasophon, Welihinda et al. 1998). There are a number of ER resident proteins, including calreticulin (CRT), which are essential for the proper implementation of these functions.

SUMMARY OF THE INVENTION

According to a first aspect of the invention, there is provided a transgenic mouse whose genome comprises
a transgene comprising a transcriptional control region operably linked to a cDNA encoding calreticulin (CRT) wherein said control region comprises a Tie-2 promoter
wherein expression of calreticulin results in spontaneously developed non-small cell tumor formation in lung, classified as adenocarcinoma. It is of note that these mice develop metastatic lung tumor which is different from other mouse models which develop only the lung tumor upon induction of lung injury.

According to a second aspect of the invention, there is provided a transgene comprising a transcriptional control region operably linked to a cDNA encoding calreticulin wherein said control region comprises a Tie-2 promoter.

According to a third aspect of the invention, there is provided a method for screening compounds that inhibit metastasis or non-small cell tumor formation in lung in a transgenic mouse comprising
providing a transgenic mouse whose genome comprises a transgene comprising a Tie-2 promoter operably linked to a cDNA encoding calreticulin (CRT);
allowing CRT to be expressed in said transgenic mouse
administering a compound to said mouse; and
determining whether said compound reduces tumor formation or metastasis.

According to a fifth aspect of the invention, there is provided a method of inhibiting tumor formation or metastasis comprising administering to an individual in need of such treatment an effective amount of virally-administered small interference RNA (siRNA) or short hairpin RNA (shRNA) corresponding to a portion of CRT mRNA, wherein expression of the siRNA (or shRNA) decreases the level of CRT. The siRNA will be generated corresponding to the following: sense 5'-GCU GAU CGU GCG GCC GGA CAA dTT 3' (SEQ ID NO:1), and anti-sense 5'-UUG UCC GGC CGC ACG AUC AGC dTT 3' (SEQ ID NO:2). This siRNA has been shown to significantly diminish the expression of CRT (Troussard et.al., 2003)

BRIEF DESCRIPTION OF THE DRAWINGS

FIG. 2 is the sequence of the Tie-2 promoter (SEQ ID NO: 3) used for generation of endothelial specific CRT overexpression.

FIG. 3 is the sequence of the Tie-2 enhancer (SEQ ID NO: 4) used for generation of endothelial specific CRT overexpression.

FIG. 13 shows the development of tumors on the cornea of the transgenic mice overexpressing calreticulin in the endothelial cells. A shows the side view of the eye from a non-transgenic mouse. B is the side view and C is the front view of the eye from a transgenic mouse. This picture shows abnormal growth on the cornea accompanied by increased angiogenesis (Arrows).

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "calreticulin" or CRT, depending on the context, refers to a peptide encoding CRT, a cDNA encoding CRT, a cDNA molecule deduced from said peptide sequence, or a bioactive fragment or mutant or variant, either inter-species or intra-species, form thereof. As will be appreciated by one of skill in the art, a variant may be CRT from a different species which has at least 60% identity, or at least 70% identity or at least 80% identity or at least 85% identity or at least 90% identity or at least 95% identity to CRT amino acid sequence or is a peptide known or believed to be related to or functionally homologous to CRT or a bioactive fragment thereof. An example of a CRT sequence may be found in SEQ ID NO: 5. As used herein, "bioactive" with regard CRT indicates that the fragment or mutant form of CRT retains substantially normal or biological CRT activity.

In a preferred embodiment, the transgene comprises a nucleotide sequence having at least 60% identity to calreticulin or at least 70% identity to calreticulin or at least 75% identity to calreticulin or at least 80% identity to calreticulin or at least 85% identity to calreticulin or at least 90% identity to calreticulin or at least 95% identity to calreticulin operably linked to an endothelial specific promoter. The endothelial specific promoter may be a mouse endothelial specific promoter. In some embodiments, the endothelial specific promoter is Tie-2, as discussed below.

In a further preferred embodiment, the transgene comprises a nucleotide sequence having at least 60% identity to mouse calreticulin or at least 70% identity to mouse calreticulin or at least 75% identity to mouse calreticulin or at least 80% identity to mouse calreticulin or at least 85% identity to mouse calreticulin or at least 90% identity to mouse calreticulin or at least 95% identity to mouse calreticulin operably linked to an endothelial specific promoter. The endothelial specific promoter may be a mouse endothelial specific promoter. In some embodiments, the endothelial specific promoter is Tie-2, as discussed below.

Figure 1:
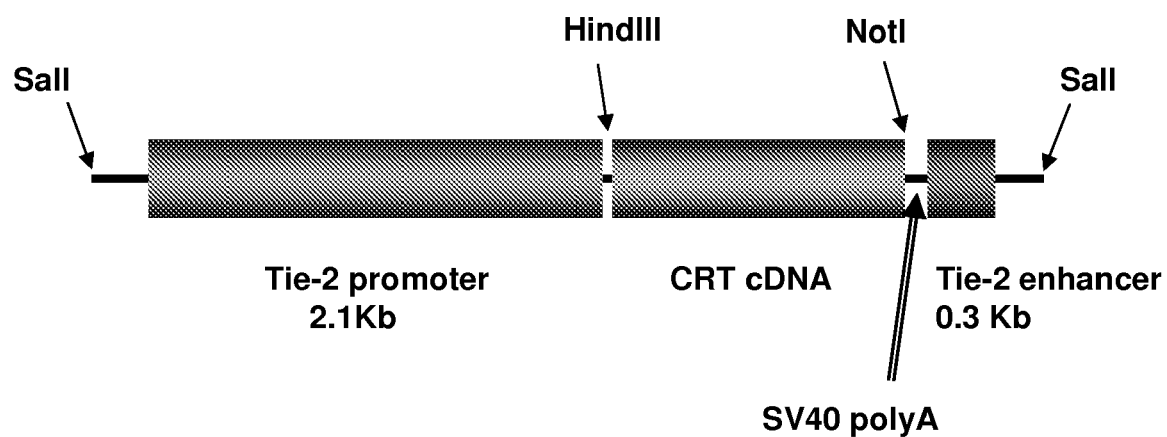
FIG. 1 is a schematic diagram of the transgene used for generation of endothelial specific CRT overexpression.

In an embodiment shown in FIG. 1, the transgene comprises Tie-2 promoter (shown in FIG. 2, nucleotides 1-2100 of SEQ ID NO: 3) operably linked to a polynucleotide encoding calreticulin (nucleotides 1-1257 of SEQ ID NO: 5). As will be apparent to one skilled in the art, SEQ ID NO: 5 corresponds to rabbit calreticulin and was used in the instant invention. The rabbit sequence has 95% identity to the mouse CRT gene and clearly has retained function, as described herein. Accordingly, it is held that the functionality of the rabbit CRT sequence in a transgenic mouse is evidence that any of the closely related CRT genes as discussed herein may be used in the invention. In some embodiments, the transgene construct includes an SV40 polyadenylation signal downstream of the calreticulin coding sequence. In yet other embodiments, the transgene construct further comprises a Tie-2 enhancer sequence, shown in FIG. 3 (nucleotides 1-303 of SEQ ID NO: 4). In some embodiments, the CRT sequence comprises an identification domain, for example, the HA sequence. As will be appreciated by one of skill in the art, the presence of the identification domain permits experimental identification of the overexpressed CRT from the endogenous CRT but is not necessarily an essential feature of the invention.

As will be appreciated by one of skill in the art, the polyA is essential for the stability of the protein in mammalian cells. In one embodiment, the enhancer is the "short form". In other embodiments, a longer form (1.7 Kb) of the Tie-2 enhancer may be used. The enhancer has been shown to be important for the uniform activation of Tie-2 promoter at both embryonic and adult stage (Schlaeger, Bartunkova et al. 1997). In absence of this enhancer Tie-2 promoter will be active only in the embryonic stages not the adult mice (Schlaeger, Qin et al. 1995).

Described herein is the preparation of a transgenic mouse arranged to express calreticulin (CRT) in endothelial cells and endothelial progenitor cells which results in the formation of spontaneous tumors primarily in the lung. These mice also develop metastatic tumors in different organs including liver, lymph nodes, spleen, eyes, optic nerve, heart, and ovary. In some mice we also observed some focal invasion of pleural cavity and intercostals muscles.

Figure 4:
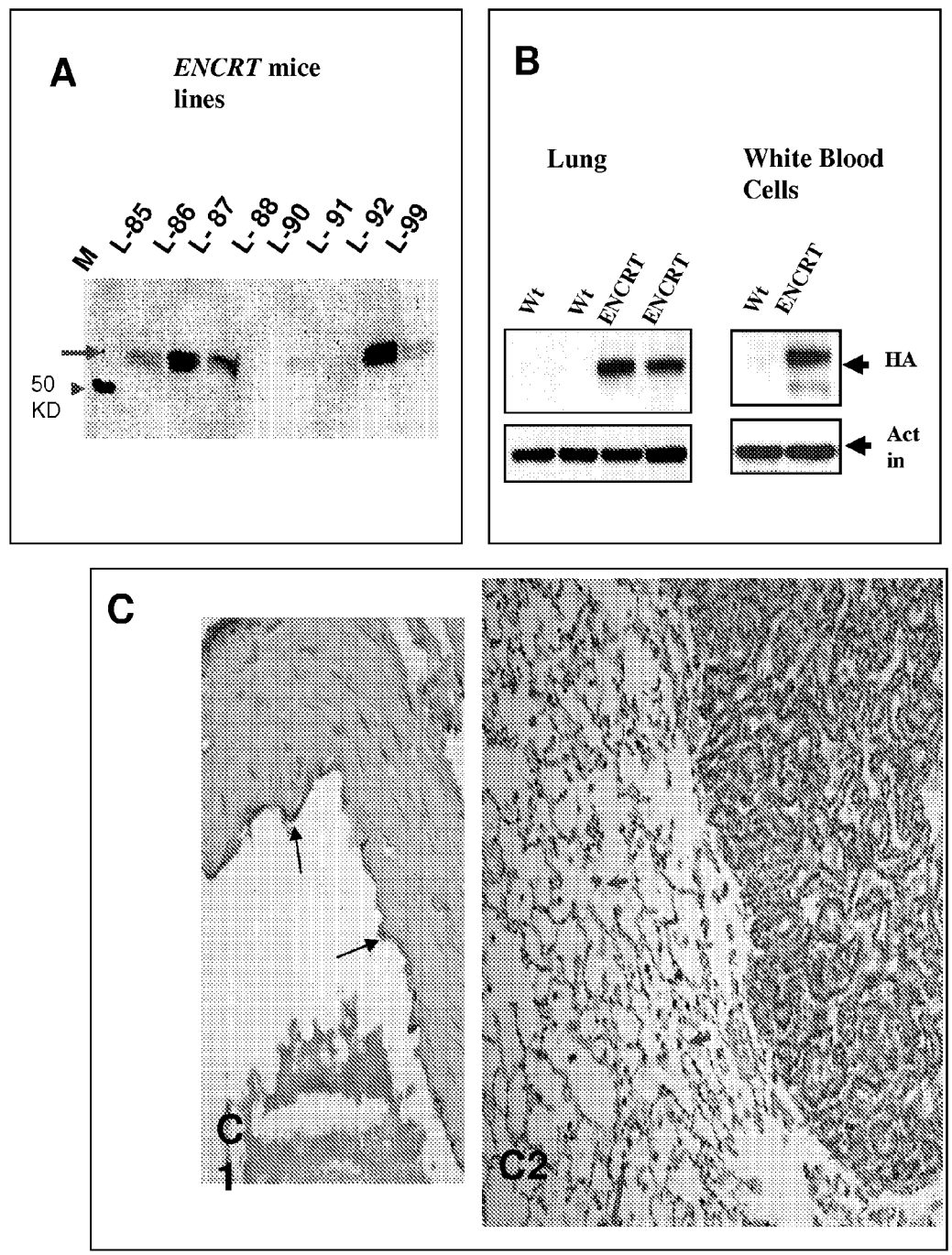
FIG. 4. A) show expression of CRT-HA in different transgenic mice lines. B) show expression of CRT-HA in the lungs and white blood cells (including circulating hematopoietic stem cells). C) shows immunohistochemistical staining of expression of CRT-HA in the endothelial cells and lung tumor (adenocarcinoma).
Figure 5:
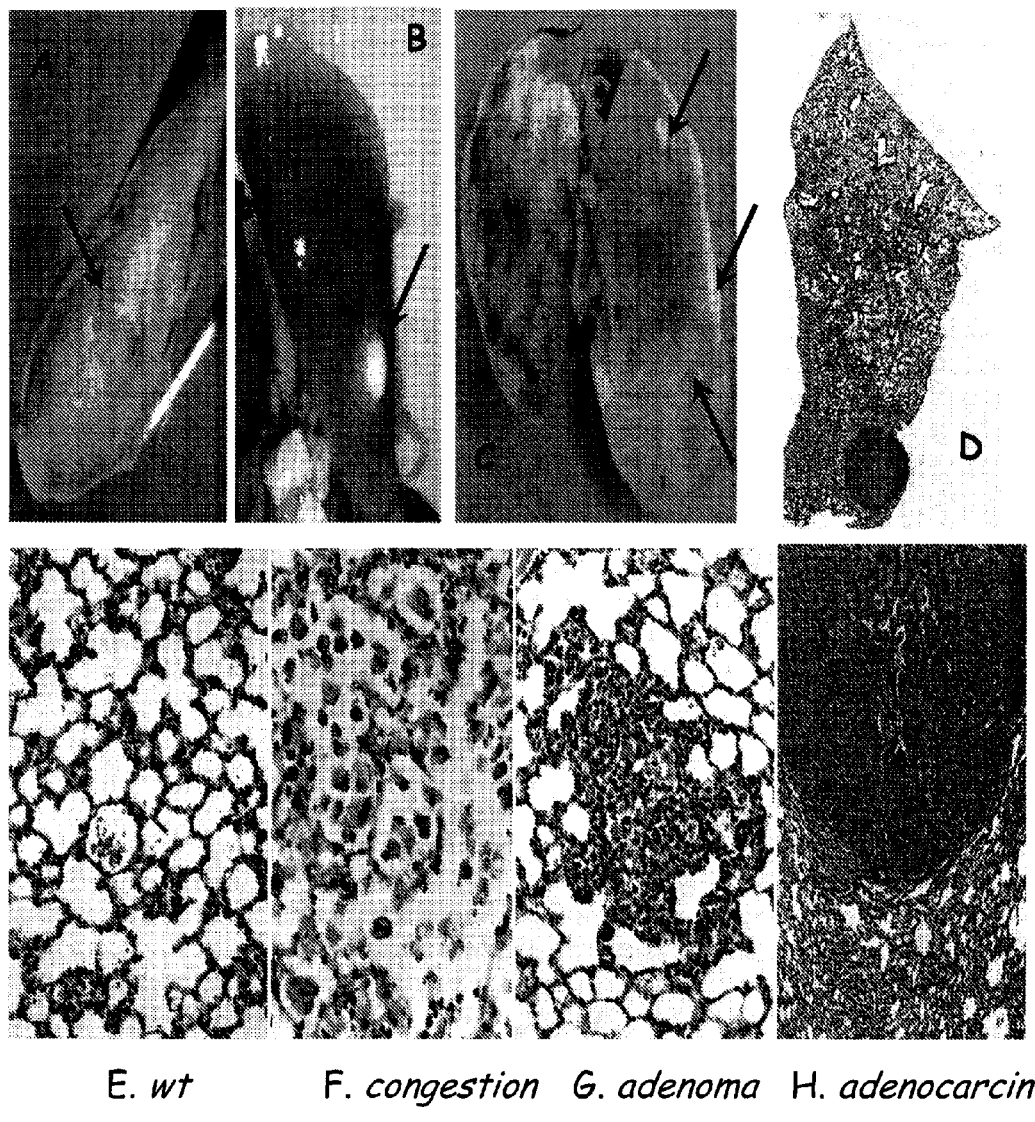
FIG. 5 shows different stages of Lung tumors developed in mice overexpressing calreticulin in endothelial cells. Arrows indicate the localized tumor in A and B. C shows lung tumor in advanced stages spreading completely in two lobes of the lung some tumors are also found in the left lobe of the lung (arrow heads). D-H show hematoxylin and eosin staining of section of lungs from different stages of lung tumour.
Figure 6:
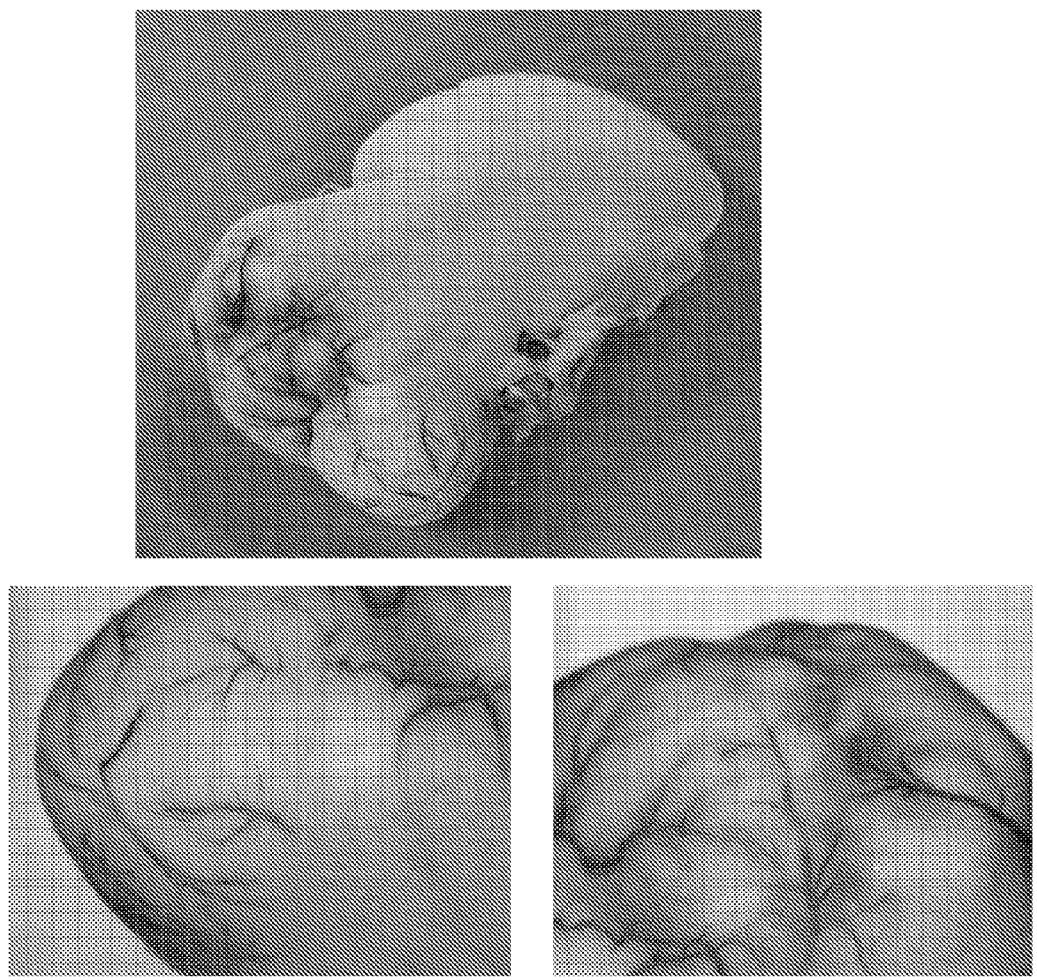
FIG. 6 shows the development of tumors in the liver of the transgenic mice overexpressing calreticulin in the endothelial cells. Liver tumor is observed in many several older mice and seems to develop subsequent to the development of the lung tumor. Lower panels are higher magnification of the tumor.
Figure 7:
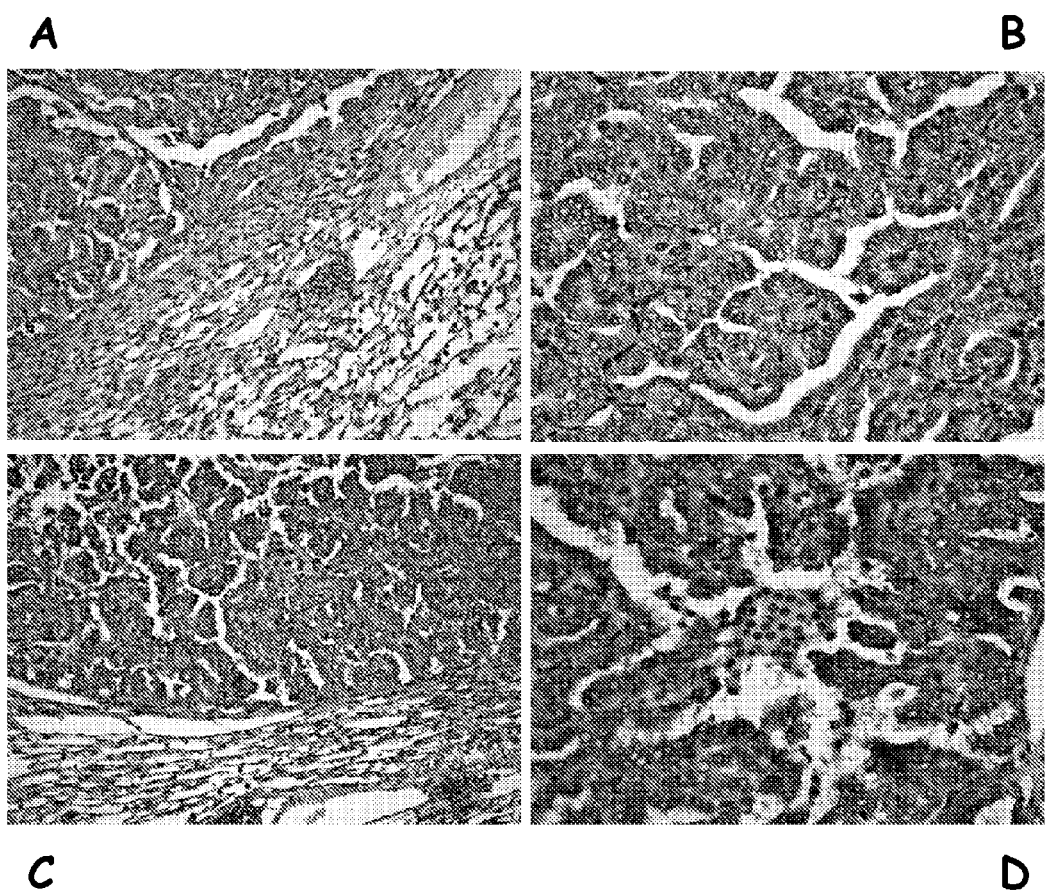
FIG. 7 shows that some cells in the lung tumor are staining with antibody to SP-C (alveolar marker). Immunohistochemical staining was carried out on 4 μm sections of paraffin embedded lung tumor. A and B are negative control (no SP-C antibody); C and D are incubated with anti-SP-C antibody. The magnification in A and C is 20× and B and D are 40×.
Figure 8:
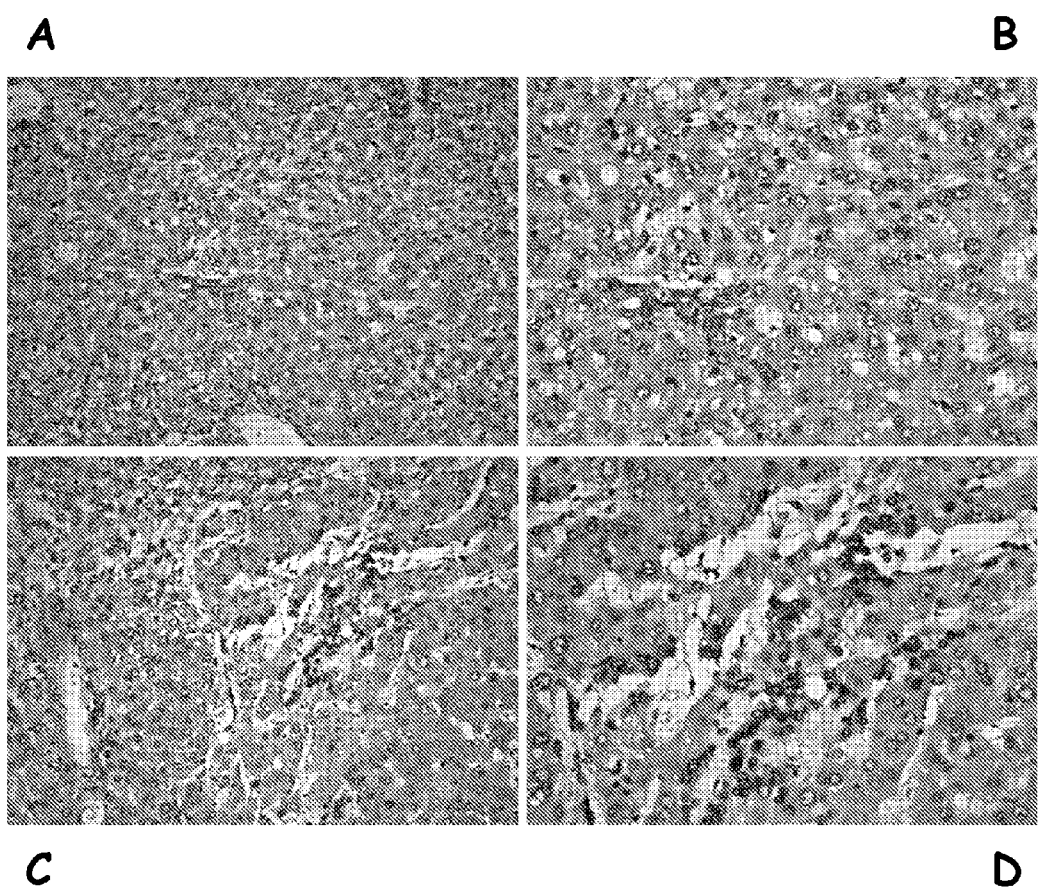
FIG. 8 shows that some cells in the liver tumor are stained with antibody to SP-C (alveolar marker). Immunohistochemical staining was carried out on 4 μm sections of paraffin embedded liver tumor. A and B are negative control (no SP-C antibody); C and D are incubated with anti-SP-C antibody. The magnification in A and C is 20× and B and D are 40×. The positive staining of SP-C in the liver indicates that the some of the tumor cells are originating from the lung.

The tumors in other organs are metastasis from the lungs to these organs. Similar spread of lung cancer to other organs has also been seen in human lung cancer patients. It is of note that in our mouse model we have observed the development of lung cancer in all of the transgenic mouse lines we have generated. We have 6 different transgenic lines each from a separate injection some with high CRT expression and some with lower level of CRT expression (FIG. 4A) yet all develop lung tumors. This eliminates any role for insertion location (gene interruption) in the development of lung tumor. The metastatic tumors are seen in most and their occurrence depends on the age of the mouse (the older the mouse, the more time to have a visible tumor in other organs). The higher the expression, the earlier we see these tumors (original and metastasis).

The development of tumor in one location usually could be cured if it is discovered early and the tumor is removed. However, the ability of the tumor to metastasize to other organs has the most detrimental effect on cancer prognosis. For a tumor to metastasize the tumor cells should detach from the original solid tumor, migrate to the blood vessel or lymphatic vessel (intravasation penetrating the vessel wall of tumor cells is also important) and finally tumor cells need to home to the new organ to start the new tumor (Chandler and G. 2004). One observation we have in our transgenic mice is that both the vascular and lymphatic vessel walls are very permeable (due to changes in the endothelial cells) which contribute to the penetration of the metastatic cells through the vessel wall to the other tissue. In addition to the increased permeability of the vessel wall, increased CRT expression can affect expression of different proteins involved in cell adhesion and cell migration (e.g. integrins, vinculin, cadherin and catenins) (Leung-Hagesteijn, Milankov et al. 1994; Opas, Szewczenko-Pawlikowski et al. 1996; Murphy-Ullrich 2001). Both of these processes (adhesion and migration) are important for lifting of the metastaic tumor cells from the solid tumor and their migration to new areas. While not wishing to be bound to a specific hypothesis, it is believed that Tie-2 driven overerxpression of CRT induces increased CRT protein in the endothelial cells, endothelial progenitor cells and haematopoietic stem cells leading to changes in the cell adhesion and migration and development of lung tumor. Previously Krause et. al., showed higher frequency of engraftment of pluripotent cells (bone marrow or haematopoietic stem cells) into lung tissue (Krause, Theise et al. 2001). Lung by nature has the largest number of endothelial (and endothelial progenitor) cells. As an organ lung is also in constant interaction with the allergens and environmental factors which can activate the engraftment of cells in it to initiate tumor growth. Thus, lungs have increased rate of recruitment of inflammatory cells. Recently, a role of chronic inflammation in recruitment of bone marrow cells has been demonstrated in development of gastric cancer (Houghton, Stoicov et al. 2004). Therefore we propose that overexpression of CRT can change the phenotype of the affected cells (endothelial cells, endothelial progenitor cells and haematopoietic stem cells) resulting in increased permeability of vessel wall and enhanced engraftment of the circulating progenitor and haematopoietic cells from the circulation in to lung tissue and increase their interaction with the surrounding lung parenchymal cells leading to the formation of tumor in the lung. The metastatic tumor cells from the lung can then invade both the vascular and the lymphatic vessels resulting in tumor metastasis to the other tissue such as liver, lymph nodes and heart.

One of the limiting factors in understanding cancer is identifying the exact cells contributing to the tumor formation. The most intriguing finding about our mouse model is that we are targeting Tie-2 expressing cells (endothelial progenitor cells, endothelial cells and hematopoietic stem cells). Our mouse model then shows a role for these specific cells in the development of lung non-small cell cancer, an observation which is novel. In cancer biology research, the role of vascular wall (and its cellular components) was thought to be limited to the delivery of blood supply to the solid tumor (via angiogenesis) and help in spreading of the metastatic cells. Thus most of research is focused on limiting rate of angiogenesis. However our transgenic mouse model demonstrates for the first time a role for endothelial cell lineage in the development of cancer.

In a preferred embodiment, the transgenic mouse prepared as described above is used for screening putative anti-metastatic agents. In these embodiments, the first step is to use MRI technology to locate the presence of tumor and its location. The animals are then treated with the chemotherapeutic agents (which are currently used in cancer treatment) and any changes in the tumor size will be followed up with subsequent MRI analysis of the tumor. In other embodiments, the effect of agents which decrease vascular permeability (e.g. anti VEGF C agents) on tumor size and metastasis are examined by administering an effective amount of these agents to the mice and monitoring tumorgenesis as discussed above. As will be appreciated by one of skill in the art, in these embodiments, tumor size and metastatic frequency in the test mouse which is administered the compound of interest may be compared to a suitable control. As will be apparent to one of skill in the art, a suitable control may be a mock-treated mouse, a mouse administered a placebo or a mouse administered a compound whose effectiveness is already known. It is also important to note that the controls do not necessarily have to be repeated each time or for each individual mouse.

In a preferred embodiment, there is provided a method of identifying an antimetastatic compound comprising administering a compound of interest to a transgenic mouse comprising calreticulin operably linked to an endothelial specific promoter as discussed above, wherein said compound of interest is an antimetastatic compound if the number of metastatic events is reduced compared to a mock-treated control mouse.

In a preferred embodiment, there is provided a method of identifying an anti-tumor compound comprising administering a compound of interest to a transgenic mouse comprising calreticulin operably linked to an endothelial specific promoter as discussed above, wherein said compound of interest is an anti-tumor compound if the size and/or number of tumors is reduced compared to a mock-treated control mouse.

We have used a plasmid containing Tie-2 promoter is called pSPTG.T2FpAXK obtained from Dr. Sato (Schlaeger, Bartunkova et al. 1997). This vector contains 2.1 Kb Tie-2 promoter region, SV40 polyA signal and Tie-2 minimum enhancer fragment (0.3 Kb) (FIG. 1). The HA tagged CRT cDNA was then cloned in the multiple cloning site of this vector (HindIII-Notl sites) upstream of SV40 polyA signal between the Tie-2 promoter and enhancer (FIG. 1). For generation of the transgenic mice, this plasmid was digested with restriction enzyme Sall to liberate the transgene DNA containing the Tie-2 promoter-CRT-HA-polyA-Tie-2minimum enhancer from the vector backbone. This piece of DNA was then injected to generate the mice.

Histological analysis of the lung tumor shows that the tumor in the lung is a non-small cell carcinoma. These tumors are negative for clara cell markers ($CC10^{31}$) and some cells in the tumor are positive for type II alveolar cells ($SPC^+$). Further histochemical analysis shows that the lung tumor is similar to human adenocarcinoma. Histological analysis of the liver and heart tumor shows that these tumors are similar to the lung tumor.

In some embodiments, the Tie-2 promoter is a 2.1 kb element as shown in FIG. 2. However, as will be appreciated by one of skill in the art, other suitable Tie-2 promoter fragments which specifically express operably linked genes in endothelial cells are known and may be used in the invention. For example, a 723 Kb of Tie-2 promoter can also be used to express genes in the endothelial cells (Minami, Kuivenhoven et al. 2003). An example of another endothelial promoter is the 3.1 Kb GATA2 promoter (Kobayashi-Osaki, Ohneda et al. 2005) which has a similar pattern of expression to the Tie-2 promoter and may be operably linked to calreticulin as discussed above.

Figure 9:
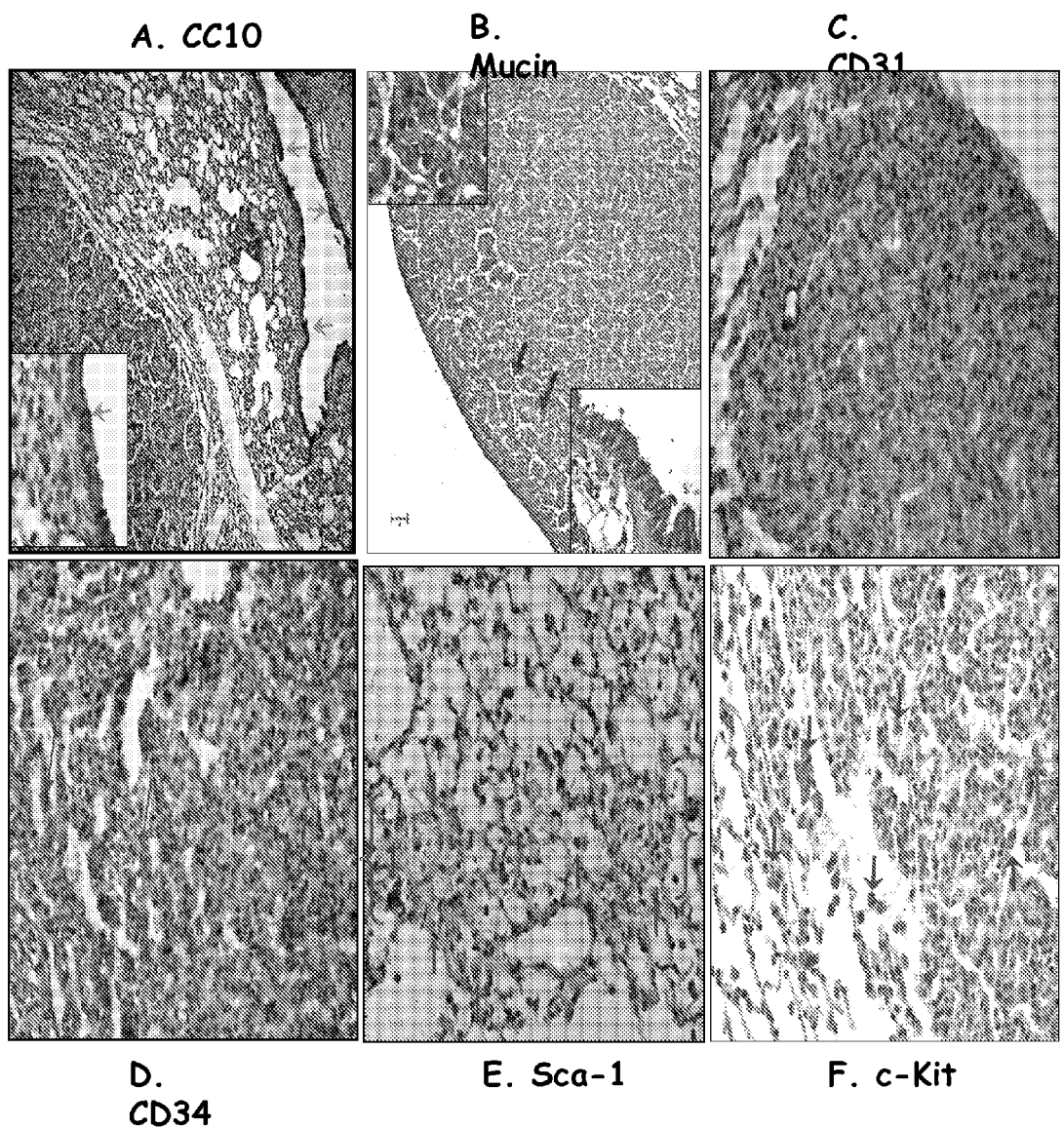
FIG. 9 shows characteristics of the lung tumors in CRT overexpressing transgenic mice. The tumor cells are CC10 negative (bronchiolar marker), mucin negative, and CD31 (PECAM, endothelial marker) negative. Some of the tumor cells stain positive with CD34, Sca-1 and c-Kit (all are markers of hematopoietic stem cells).
Figure 10:
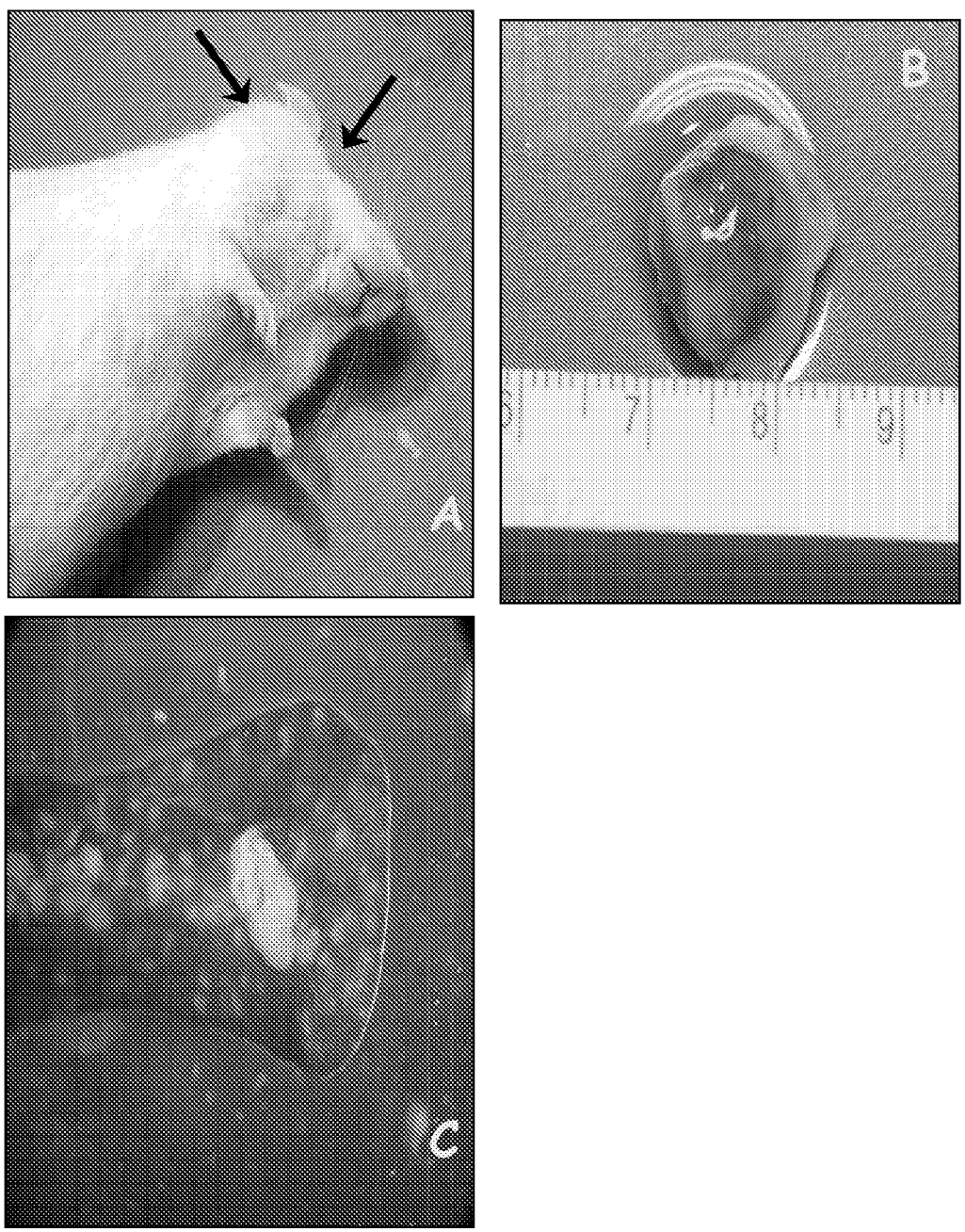
FIG. 10 shows the development of metastatic tumors in the sublingual lymph node of an CRT overexpressing transgenic mouse. Metastasis to abdominal lymph nodes, subcutaneous lymphnode and lymph nodes in the chest were also observed.
Figure 11:
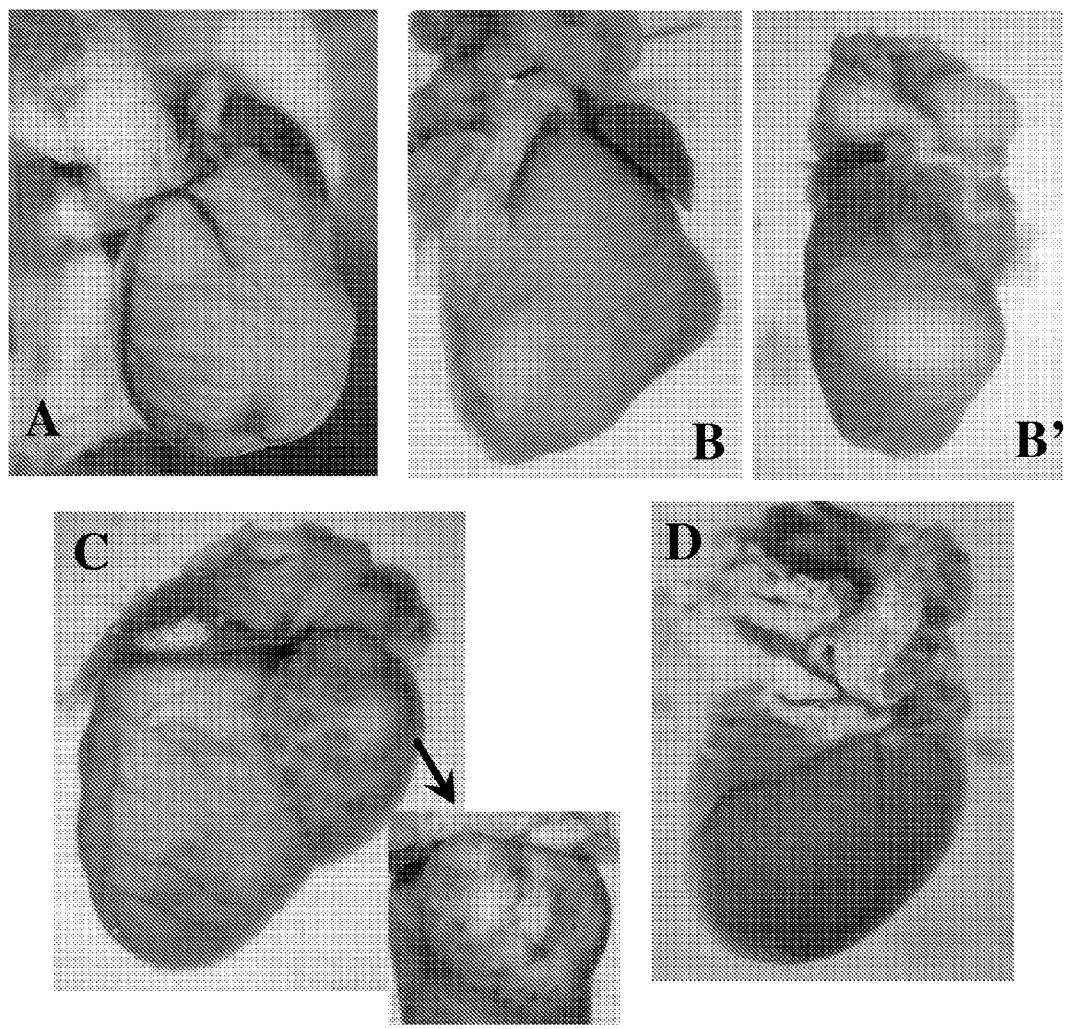
FIG. 11 shows the development of metastatic tumors in the heart (atria and ventricles) of transgenic mice overexpressing calreticulin in the endothelial cells. A, B, C are hearts isolated from mice from three different lines. D is the heart isolated from a non-transgenic mouse. B and B' are the same heart from different angels showing the ventricular tumor. C inset is a side view of the tumor developed in the atria.
Figure 12:
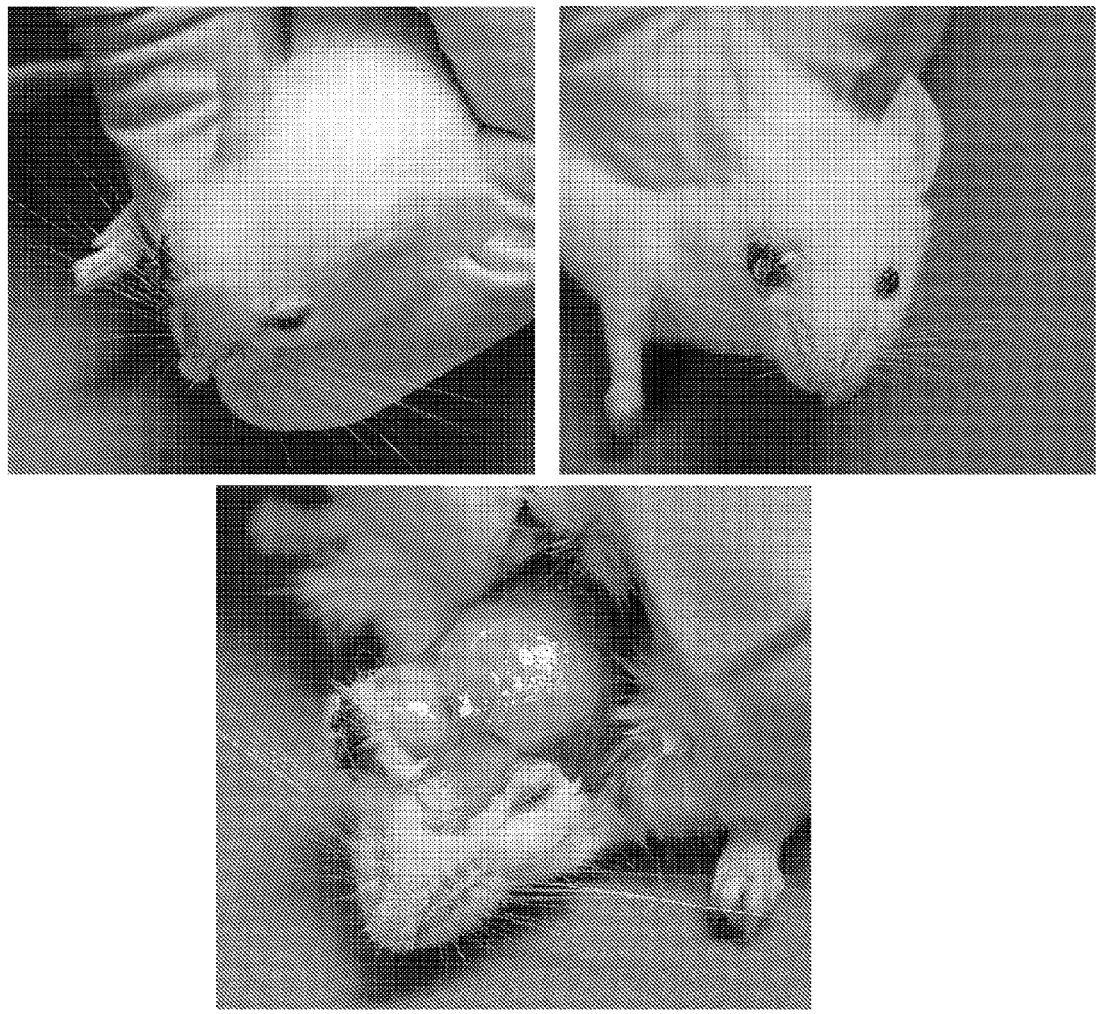
FIG. 12 shows the development of metastatic tumors in the optic nerve of transgenic mice overexpressing calreticulin in the endothelial cells. In addition to the development of the tumor the cornea is also affected in this animal.

It is essential to determine the cellular composition of the lung tumor and compare the cell types in these tumors to the cell types in the tumor in the other tissues (to determine if they are metastasis). Indeed in our preliminary experiments we determined that the lung tumors are CC10 negative (a protein found in the epithelial cells of the bronchioles and trachea) and some of the cells are positive for SP-C (alveolar marker). Interestingly staining the liver tumors showed the presence of some positively SP-C stained cells, confirming their lung origin (and metastasis from lung to the liver). The lung of the CRT overexpressing transgenic mice were also stained for stem cell markers; c-kit, Sca1; and CD34, endothelial markers (PECAM and vWF), and HA antibody using immunohistochemical staining. The tumour cells were positive for HA. Some of the cells in the tumour and the circulating cells found in the alveolar spaces of the lung in our transgenic mice stained positive for Sca-1, c-Kit, and CD34 (FIG. 9). The expression of SP-C and all the above proteins will also be tested in the other tumors found in these animals. These tumors will also be characterized for expression of many cell cycle regulatory genes which have been reported to be involved in the development of cancer e.g. p53, ras, p16$^{INK4A}$, p14$^{ARF}$, myc and cell proliferation marker Ki67. To examine changes in gene expression profile in the lungs (and the metastatic tumors e.g. livers and lymph nodes) of these transgenic mice we will carry out microarray analysis. The genes which show over 2 fold change in their expression will then be confirmed by western blot analysis. Calreticulin is an endoplasmic reticular chaperone therefore alteration in its expression could affect the proper folding and processing of many proteins. To test if there are any changes in at the protein level without effect on the gene expression we will carry out proteomic analysis of the lung tissue (tissue composed of tumor alone, surrounding lung tissue and lung from and nontransgenic litter mate) using 2D gels and MALDI-TOF mass spectrometry.

One of the main reasons for poor outcome of lung cancer is due to its late diagnosis. Therefore, it is important to identify markers for lung tumor as early as possible. Our mouse model could be used to identify any early markers of lung tumor and metastasis. For this end we will examine serum protein profile of the transgenic and non-transgenic littermates at three different time points (before appearance of any lung lesion, in early stages of development of lung tumor and at fully developed metastatic lung tumor stage) using proteomic techniques. These experiments will be carried out in the 6 mouse models we have in our lab to test their reproducibility. On longer run we will also obtain serum samples from non-small cell lung tumor patients. The profile of protein expression in the patient serum will be compared to the profile obtained from the mouse with tumor in similar stage as the patient. These analyses could potentially identify markers which could be used for screening at a high throughput fashion.

In order to examine the signalling pathways activated in the lung tumor cells we have established cell lines from the tumors of our transgenic mice. These cells will be used for analysis of the response to different chemotherapeutical treatment and response to radiation. These cells will also be used for dissecting the changes in many different signalling pathways important for increased cell division and inhibition of apoptosis.

In one embodiment of the invention, there is provided a transgenic mouse whose genome comprises a transgene comprising a transcriptional control region operably linked to a cDNA encoding calreticulin (CRT) wherein said control region comprises a promoter wherein expression of calreticulin in the vascular wall results in hemangioma formation. In some embodiments, the promoter is the Tie-2 promoter. In other embodiments, the cDNA sequence within the transgene may include sequence variations, for example, mutations and deletions, which do not significantly affect or alter the normal, biological function of CRT, in this case, the expression of CRT resulting in tumor formation.

In another embodiment of the invention, there is provided a transgene comprising a transcriptional control region operably linked to a cDNA encoding calreticulin as defined above wherein said control region comprises a Tie-2 promoter. As discussed above, in some embodiments, the transgene may include an enhancer.

In another aspect of the invention, there is provided a method for producing a transgenic mouse whose genome comprises CRT comprising: introducing into a fertilized mouse egg a transgene comprising a transcriptional control region operably linked to a cDNA encoding CRT wherein said control region comprises a promoter; transplanting the injected egg in a foster parent female mouse; and selecting a mouse derived from an injected egg whose genome comprises CRT. As will be appreciated by one of skill in the art, the transgene may be introduced into the mouse egg by any of a number of suitable methods known in the art.

In another embodiment of the invention, there is provided a method for screening compounds that inhibit tumor metastasis in a transgenic mouse comprising providing a transgenic mouse whose genome comprises a transgene comprising a transcriptional control region operably linked to a cDNA encoding calreticulin (CRT); allowing CRT to be expressed in said transgenic mouse administering a compound to said mouse; and determining whether said compound reduces tumor metastasis. In these embodiments, the metastasis in the mouse treated with the compound may be compared to metastasis in an untreated control and the difference between the treated mouse and untreated control used to determine efficacy of the compound.

Studies on the molecular changes in cancer have been focused on utilizing tumor cell lines derived from human cancers during surgery. While these are important tools for understanding changes in cancer cells, they are not useful in studying the mechanism of development of tumor metastasis (Chandler and G. 2004). Many scientists have used techniques to implant cancer cell lines and modified cancer cell lines in nude mice in a trial to study the metastatic process. More recently, following success in the techniques for manipulation of mouse genome, transgenic mouse models have become a strong tool to understand the role of each gene and cell type in the formation of tumor and the metastatic process (Schlaeger, Bartunkova et al. 1997).

In another embodiment of the invention, there is provided a method of inhibiting metastasis comprising administering to an individual in need of such treatment an effective amount of virally-administered small interference RNA (siRNA) or short hairpin RNA (shRNA) corresponding to a portion of CRT mRNA, wherein expression of the siRNA (shRNA) decreases the level of CRT. Efficient and stable expression of shRNA can be achieved by gene delivery using means known in the art, for example, using lentiviral plasmids which are available commercially (Invitrogen).

In another embodiment of the invention, there is provided a method of testing the therapeutic activity of a pharmacological agent on metastasis or non-small cell lung carcinoma comprising administering an effective amount of said pharmacological agent to the above-described transgenic mouse and evaluating said agent's effect on metastasis and/or lung tumor formation of said mouse. As will be appreciated by one of skill in the art, the evaluation may comprise detecting for example a decrease in tumor size or metastatic frequency or formation compared to an untreated or mock-treated control. It is important to note that in the process, the control does not necessarily need to be repeated with each trial. It is of note that the pharmacological agent may be for example a peptide or peptide fragment, a small molecule, a chemical compound, a nucleic acid or the like.

CRT is a ubiquitous eukaryotic protein which shares a high degree of identity among all the different species (Michalak 1996). CRT is the product of translation of a single mRNA (Michalak 1996), resulting in a 46 kDa protein which is localized to the lumen of ER and nuclear envelope (Michalak, Milner et al. 1992; Milner, Famulski et al. 1992; Michalak 1996). Several unique functions have been postulated for CRT (reviewed in (Michalak, Corbett et al. 1999), including chaperone activity (Nigam, Goldberg et al. 1994; Nauseef, McCormick et al. 1995; Hebert, Zhang et al. 1997), regulation of cell adhesion (Coppolino, Leung-Hagesteijn et al. 1995; Opas, Szewczenko-Pawlikowski et al. 1996; Coppolino, Woodside et al. 1997), modulation of steroid mediated gene expression (Burns, Duggan et al. 1994; Dedhar, Rennie et al. 1994; Wheeler, Horsford et al. 1995; Winrow, Miyata et al. 1995; Michalak, Burns et al. 1996), and regulation of $Ca^{2+}$ homeostasis (Liu, Fine et al. 1994; Bastianutto, Clementi et al. 1995; Camacho and Lechleiter 1995; Mery, Mesaeli et al. 1996; Coppolino, Woodside et al. 1997).

Chaperone function of CRT—CRT is a lectin-like chaperone (Hammond and Helenius 1995; Peterson, Ora et al. 1995; Spiro, Zhu et al. 1996), involved in the "quality control" process during the synthesis and folding of a variety of proteins including cell surface receptors, integrins and transporters (Helenius, Trombetta et al. 1997). CRT binds the terminal glucose of the oligosaccharide moiety of the unfolded protein. During the folding process, the newly synthesized protein can go through many cycles of binding and release from the lectin-like chaperone by removal and addition of this terminal glucose (involving glucosidase I and II, and UDP-glucose transferase, respectively). This results in the proper processing of the protein. If the protein is misfolded, it will accumulate in the cell triggering an "unfolded protein response" and starting protein degradation. In the CRT null mouse embryonic fibroblast cells, we have observed an increase in the expression of a number of ER chaperones; however the function of these chaperones seems to be compromised (Mesaeli, Ahsan et al. 2000). Indeed, the unfolded protein response in these cells is stimulated as evident by a significant (100%) increase in the expression of BiP (Grp78) (Mesaeli, Ahsan et al. 2000). CRT has been shown to be bind to glycosylated laminin in the ER (McDonnell, Jones et al. 1996) perhaps affecting its folding. Overexpression of CRT has been shown to increase the level of pro-MMP2 protein (Ito, Seyama et al. 2001). Other proteins which have been shown to be malformed in absence of CRT includes: bradykinin receptor (Nakamura, Zuppini et al. 2001), MHC class I protein (Gao, Adhikari et al. 2002), Myeloperoxidase (Nauseef, McCormick et al. 1995; Nauseef, McCormick et al. 1998) $IP_3$ receptor (all three isoforms) (Paziuk and Mesaeli 2002), and connexin 43 protein which fails to localize to the cell-cell junction in the heart (Ahmadi, Kardami et al. 2002). Interestingly, overexpression of CRT in the hearts of transgenic mice resulted in a decrease in the expression of connexin 40 and 43 (Nakamura, Robertson et al. 2001).

CRT and cell adhesion—The first evidence for the possible role of CRT in cell adhesion came from in vitro studies designed to identify the cellular proteins which bind to KxFF(k/R)R peptide (Rojiani, Finlay et al. 1991), a consensus sequence in the C-terminal tail of the α-subunit of integrin. However, recent reports indicate that CRT may influence cell adhesion indirectly via modulation of gene expression of adhesion related molecules (Opas, Szewczenko-Pawlikowski et al. 1996; Fadel, Dziak et al. 1999), or by changes in the integrin-dependent $Ca^{2+}$ signaling (Coppolino, Woodside et al. 1997). Overexpression of CRT results in up-regulation of vinculin and N-cadherin (Opas, Szewczenko-Pawlikowski et al. 1996; Fadel, Dziak et al. 1999), resulting in an increase in cell-substratum attachment. Down regulation of CRT results in an opposite effect (Leung-Hagesteijn, Milankov et al. 1994; Opas, Szewczenko-Pawlikowski et al. 1996). Protein tyrosine phosphorylation/dephosphorylation comprises one of the major mechanisms in regulating cell adhesion (Burridge and Chrzanowska-Wodnicka 1996), (Daniel and Reynolds 1997; Cox and Huttenlocher 1998). Previously, we have reported a significant decrease in the level of tyrosine phosphorylation in fibroblast cells overexpressing CRT (Fadel, Dziak et al. 1999) which coincided with changes in cell adhesiveness.

CRT and intracellular $Ca^{2+}$—CRT was initially discovered as a $Ca^{2+}$ binding protein in the lumen of ER (Ostwald, MacLennan et al. 1974), (Michalak, Campbell et al. 1980). The protein has two $Ca^{2+}$ binding sites: a high affinity, low capacity site and a low capacity, high affinity site (Ostwald, MacLennan et al. 1974), (Baksh and Michalak 1991). Overexpression of CRT results in an increased level of intracellular $Ca^{2+}$, however, it does not affect the cytosolic free $Ca^{2+}$ concentration (Bastianutto, Clementi et al. 1995), (Mery, Mesaeli et al. 1996), (Michalak, Burns et al. 1996; Opas, Szewczenko-Pawlikowski et al. 1996). Knockout of the CRT gene did not result in a change in the $Ca^{2+}$ storage capacity of the ER in ES cells and in mouse embryonic fibroblast cells (Coppolino, Woodside et al. 1997; Mesaeli, Nakamura et al. 1999). However, CRT deficient mouse embryonic fibroblast cells have decreased agonist-mediated $IP_3$-dependent $Ca^{2+}$ release from ER (Mesaeli, Nakamura et al. 1999). CRT deficient ES cells also showed a defect in integrin mediated $Ca^{2+}$ signaling (Coppolino, Woodside et al. 1997). These results suggest a change in the expression of CRT can alter cellular $Ca^{2+}$ homeostasis which in turn can affect many cell signaling pathways including cell adhesion (via integrin).

REFERENCES

Ahmadi, S., E. Kardami, et al. (2002). "Altered connexin 43 localization in calreticulin knockout mice." *Mol. Biol. Cell* 13: 1209.

Baksh, S. and M. Michalak (1991). "Expression of calreticulin in *Escherichia coli* and identification of its Ca2+ binding domains." *J Biol Chem* 266(32): 21458-65.

Bastianutto, C., E. Clementi, et al. (1995). "Overexpression of calreticulin increases the Ca2+ capacity of rapidly exchanging Ca2+ stores and reveals aspects of their lumenal microenvironment and function." *J Cell Biol* 130(4): 847-55.

Burns, K., B. Duggan, et al. (1994). "Modulation of gene expression by calreticulin binding to the glucocorticoid receptor." *Nature* 367(6462): 476-80.

Burridge, K. and M. Chrzanowska-Wodnicka (1996). "Focal adhesions, contractility, and signaling." *Annu Rev Cell Dev Biol* 12: 463-518.

Camacho, P. and J. D. Lechleiter (1995). "Calreticulin inhibits repetitive intracellular Ca2+ waves." *Cell* 82(5): 765-71.

Chandler, D. S. and L. G. (2004). Metastasis. *Mouse Models of Human Cancer*. E. C. Holland. New Jersey, John Wiley-Liss: 307-320.

Coppolino, M., C. Leung-Hagesteijn, et al. (1995). "Inducible interaction of integrin alpha 2 beta 1 with calreticulin. Dependence on the activation state of the integrin." *J Biol Chem* 270(39): 23132-8.

Coppolino, M. G., M. J. Woodside, et al. (1997). "Calreticulin is essential for integrin-mediated calcium signalling and cell adhesion." *Nature* 386(6627): 843-7.

Cox, E. A. and A. Huttenlocher (1998). "Regulation of integrin-mediated adhesion during cell migration." *Microsc Res Tech* 43(5): 412-9.

Daniel, J. M. and A. B. Reynolds (1997). "Tyrosine phosphorylation and cadherin/catenin function." *Bioessays* 19(10): 883-91.

Dedhar, S., P. S. Rennie, et al. (1994). "Inhibition of nuclear hormone receptor activity by calreticulin." *Nature* 367 (6462): 480-3.

Fadel, M. P., E. Dziak, et al. (1999). "Calreticulin affects focal contact-dependent but not close contact-dependent cell-substratum adhesion." *J Biol Chem* 274(21): 15085-94.

Gao, B., R. Adhikari, et al. (2002). "Assembly and antigen-presenting function of MHC class I molecules in cells lacking the ER chaperone calreticulin." *Immunity* 16(1): 99-109.

Hammond, C. and A. Helenius (1995). "Quality control in the secretory pathway." *Curr Opin Cell Biol* 7(4): 523-9.

Hebert, D. N., J. X. Zhang, et al. (1997). "The number and location of glycans on influenza hemagglutinin determine folding and association with calnexin and calreticulin." *J Cell Biol* 139(3): 613-23.

Helenius, A., E. S. Trombetta, et al. (1997). "Calnexin, calreticulin and the folding of glycoproteins." *Trends in Cell Biology* 7: 193-200.

Houghton, J., C. Stoicov, et al. (2004). "Gastric cancer originating from bone marrow-derived cells." *Science* 306(5701): 1568-71.

Ito, H., Y. Seyama, et al. (2001). "Calreticulin is directly involved in anti-alpha3 integrin antibody-mediated secretion and activation of matrix metalloprotease-2." *Biochem Biophys Res Commun* 283(2): 297-302.

Kobayashi-Osaki, M., O. Ohneda, et al. (2005). "GATA motifs regulate early hematopoietic lineage-specific expression of the Gata2 gene." *Mol Cell Biol* 25(16): 7005-20.

Krause, D. S., N. D. Theise, et al. (2001). "Multi-organ, multi-lineage engraftment by a single bone marrow-derived stem cell." *Cell* 105(3): 369-77.

Leung-Hagesteijn, C. Y., K. Milankov, et al. (1994). "Cell attachment to extracellular matrix substrates is inhibited upon downregulation of expression of calreticulin, an intracellular integrin alpha-subunit-binding protein." *J Cell Sci* 107(Pt 3): 589-600.

Liu, N., R. E. Fine, et al. (1994). "Decreasing calreticulin expression lowers the Ca2+ response to bradykinin and increases sensitivity to ionomycin in NG-108-15 cells." *J Biol Chem* 269(46): 28635-9.

McDonnell, J. M., G. E. Jones, et al. (1996). "Calreticulin binding affinity for glycosylated laminin." *J Biol Chem* 271(14): 7891-4.

Mery, L., N. Mesaeli, et al. (1996). "Overexpression of calreticulin increases intracellular Ca2+ storage and decreases store-operated Ca2+ influx." *J Biol Chem* 271 (16): 9332-9.

Mesaeli, N., I. Ahsan, et al. (2000). "Endoplasmic reticulum chaperones in calreticulin deficient mouse embryonic fibroblasts cells." *Molecular Biology of the cell* 11: 491a.

Mesaeli, N., K. Nakamura, et al. (1999). "Calreticulin is essential for cardiac development." *J Cell Biol* 144(5): 857-68.

Michalak, M. (1996). *Calreticulin*. Austin, Texas, R. G. Landes Company.

Michalak, M., K. Burns, et al. (1996). "Endoplasmic reticulum form of calreticulin modulates glucocorticoid-sensitive gene expression." *J Biol Chem* 271(46): 29436-45.

Michalak, M., K. P. Campbell, et al. (1980). "Localization of the high affinity calcium binding protein and an intrinsic glycoprotein in sarcoplasmic reticulum membranes." *J Biol Chem* 255(4): 1317-26.

Michalak, M., E. F. Corbett, et al. (1999). "Calreticulin: one protein, one gene, many functions [In Process Citation]." *Biochem J* 344 Pt 2: 281-92.

Michalak, M., R. E. Milner, et al. (1992). "Calreticulin." *Biochem J* 285(Pt 3): 681-92.

Milner, R. E., K. S. Famulski, et al. (1992). "Calcium binding proteins in the sarcoplasmic/endoplasmic reticulum of muscle and nonmuscle cells." *Mol Cell Biochem* 112(1): 1-13.

Minami, T., J. A. Kuivenhoven, et al. (2003). "Ets motifs are necessary for endothelial cell-specific expression of a 723-bp Tie-2 promoter/enhancer in Hprt targeted transgenic mice." *Arterioscler Thromb Vasc Biol* 23(11): 2041-7.

Murphy-Ullrich, J. E. (2001). "The de-adhesive activity of matricellular proteins: is intermediate cell adhesion an adaptive state?" *J Clin Invest* 107(7): 785-90.

Nakamura, K., M. Robertson, et al. (2001). "Complete heart block and sudden death in mice overexpressing calreticulin." *J Clin Invest* 107(10): 1245-53.

Nakamura, K., A. Zuppini, et al. (2001). "Functional specialization of calreticulin domains." *J Cell Biol* 154(5): 961-72.

Nauseef, W. M., S. J. McCormick, et al. (1995). "Calreticulin functions as a molecular chaperone in the biosynthesis of myeloperoxidase." *J Biol Chem* 270(9): 4741-7.

Nauseef, W. M., S. J. McCormick, et al. (1998). "Coordinated participation of calreticulin and calnexin in the biosynthesis of myeloperoxidase." *J Biol Chem* 273(12): 7107-11.

Nigam, S. K., A. L. Goldberg, et al. (1994). "A set of endoplasmic reticulum proteins possessing properties of molecular chaperones includes Ca(2+)-binding proteins and members of the thioredoxin superfamily." *J Biol Chem* 269(3): 1744-9.

Opas, M., M. Szewczenko-Pawlikowski, et al. (1996). "Calreticulin modulates cell adhesiveness via regulation of vinculin expression." *J Cell Biol* 135(6 Pt 2): 1913-23.

Ostwald, T. J., D. H. MacLennan, et al. (1974). "Effects of cation binding on the conformation of calsequestrin and the high affinity calcium-binding protein of sarcoplasmic reticulum." *J Biol Chem* 249(18): 5867-71.

Paziuk, T. and N. Mesaeli (2002). "Impaired Ca release by P2Y receptor in calreticulin null cells is due to altered IP3 receptor expression." *Journal of Molecular Cellular Cardiology* 34(7): A19-01.

Peterson, J. R., A. Ora, et al. (1995). "Transient, lectin-like association of calreticulin with folding intermediates of cellular and viral glycoproteins." *Mol Biol Cell* 6(9): 1173-84.

Pozzan, T., R. Rizzuto, et al. (1994). "Molecular and cellular physiology of intracellular calcium stores." *Physiol Rev* 74(3): 595-636.

Rojiani, M. V., B. B. Finlay, et al. (1991). "In vitro interaction of a polypeptide homologous to human Ro/SS-A antigen (calreticulin) with a highly conserved amino acid sequence in the cytoplasmic domain of integrin alpha subunits." *Biochemistry* 30(41): 9859-66.

Schlaeger, T. M., S. Bartunkova, et al. (1997). "Uniform vascular-endothelial-cell-specific gene expression in both embryonic and adult transgenic mice." *Proc Natl Acad Sci U S A* 94(7): 3058-63.

Schlaeger, T. M., Y. Qin, et al. (1995). "Vascular endothelial cell lineage-specific promoter in transgenic mice." *Development* 121(4): 1089-98.

Spiro, R. G., Q. Zhu, et al. (1996). "Definition of the lectin-like properties of the molecular chaperone, calreticulin, and demonstration of its copurification with endomannosidase from rat liver Golgi." *J Biol Chem* 271(19): 11588-94.

Tirasophon, W., A. A. Welihinda, et al. (1998). "A stress response pathway from the endoplasmic reticulum to the nucleus requires a novel bifunctional protein kinase/endoribonuclease (Ire1p) in mammalian cells." *Genes Dev* 12(12): 1812-24.

Welihinda, A. A., W. Tirasophon, et al. (1997). "Gene induction in response to unfolded protein in the endoplasmic reticulum is mediated through Ire1p kinase interaction with a transcriptional coactivator complex containing Ada5p." *Proc Natl Acad Sci U S A* 94(9): 4289-94.

Wheeler, D. G., J. Horsford, et al. (1995). "Calreticulin inhibits vitamin D3 signal transduction." *Nucleic Acids Res* 23(16): 3268-74.

Winrow, C. J., K. S. Miyata, et al. (1995). "Calreticulin modulates the in vitro DNA binding but not the in vivo transcriptional activation by peroxisome proliferator-activated receptor/retinoid X receptor heterodimers." *Mol Cell Endocrinol* 111(2): 175-9.

The invention claimed is:

1. A transgenic mouse whose genome comprises a transgene comprising a Tie-2 promoter operably linked to a cDNA encoding calreticulin (CRT) wherein expression of calreticulin in endothelial cells of the mouse results in non-small cell tumor formation in lungs.

2. A transgene comprising a transcriptional control region operably linked to a cDNA encoding calreticulin wherein said control region comprises a Tie-2 promoter.

3. A method for screening compounds that inhibit non-small cell tumor formation in lung or metastasis in a transgenic mouse comprising providing a transgenic mouse whose genome comprises a transgene comprising a Tie-2 promoter operably linked to a cDNA encoding calreticulin (CRT);

allowing CRT to be expressed in said transgenic mouse administering a compound to said mouse; and determining whether said compound reduces tumor formation or metastasis.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: artificial
<220> FEATURE:
<223> OTHER INFORMATION: small interference RNA or short hairpin RNA for
      decreasing calreticulin levels

<400> SEQUENCE: 1
gcugaucgug cggccggaca att                                             23

<210> SEQ ID NO 2
<211> LENGTH: 23
<212> TYPE: DNA
<213> ORGANISM: artificial
<220> FEATURE:
<223> OTHER INFORMATION: small interference RNA or short hairpin RNA for
      reducing calreticulin levels

<400> SEQUENCE: 2
uuguccggcc gcacgaucag ctt                                             23

<210> SEQ ID NO 3
<211> LENGTH: 2100
<212> TYPE: DNA
<213> ORGANISM: mouse

<400> SEQUENCE: 3
agtggatgag gtttagtgtt aggcattcag gaaatagagt aaaaggaaat gaattatggt     60
catcaggtgc taggtgtgtg tgtgtgtgtg tgtgtgtgtg tgtgtgtgta              120
tgactgacat cacctataag acctgtaagt attttatggt atttagtctt tatcgggcaa    180
aggacttacc agcaccactg taaagatgat gtaaatgagc ccagagggag atgaagtgtt    240
tccttagaca tcatctcgct aatctcgata agaacttaat gtggaaccat agtaatattt    300
ttctgaaaat atctcctgct tttgaagaga ctggactttt gccagactac aactaagttt    360
gtaatatact ctgaggttac ttaagtctat gtattcaatc tgctgtccta ccgtgtactg    420
tgccttctaa ctggtttaac ctgcctttaa gaaagcaatg taagtgaccc ttaccctgcc    480
ttggatttcc catgcaatca gcttttatac cctaaggcaa tgcatagttt taatcttaac    540
taggtactct ccacacccct gaccatgaat aatctacata tgtgtgtata ctgtggtaat    600
```

-continued

```
aatatgctga aagcagccat caggttgaga acaaccttaa acaacaaaca ctgtaacagt      660
tcaaagcaac atggatgtag gttgattaca tcttcacgtg gttttaggtg ctattctgga      720
gtactaaagt ttcccctgtg tacaactctt aaaattcact gtctagacgt atcccgcgtg      780
ccttccccta ccatgctttc tgtgctgttc aataaatacg gagcagagcc ctttgttaca      840
acagggaaca tagacagaca gctaggacag acacaagtaa aacatgtata acagcccggt      900
aatacagaca gacctcaggc caagtttcac acagattttt cctagggaga gggatggcct      960
tgctcttggt ctaaactact ccaagaggaa gtctcttttg tcaccatttt tgtgacactg     1020
acacattttg tcgccccctc cacccccccc ccccccgctc ttctgagttt ttttaaataa     1080
tattttgaaa atgaaggtct ataaagttag cataagtgga tatagttgtt gatacagacc     1140
tttagtgtgc ttagtgggca gtattctaaa atcaattcac taattaaaaa ctaataatga     1200
taatttatta ataatattat actatcttca tttcttagct taattgagca agcatttaat     1260
taatgcctaa ctatgcctca atcaatatag tagagcatat attgtacata catacttgta     1320
cacacacaca cacacacaca cacacacaca cacacacaca cacattatgt tcaagtctat     1380
tgcagatcag gtatgcagtg gggaagtgga agaagtaagg tctagcagat gaaaggactt     1440
gattccttgg taaagaattt tgattctgtc cagtgggata caggcacatg atcagaacat     1500
tttaaaatga ttgttcatat aactattttt tattaattaa ttattttatt tatttatatc     1560
cctaatgtta ccctctccag gtccccccett gcagagttct tctccccatc cccctttcct     1620
tcacctctga gagggtaccc ccccccaag ggggcatca agtctctaca ggattaggtg       1680
tatcccattg aggccagaca agaagttgt ctgctacatg tgcaaggggc ccttggacca      1740
gcccatgtat gctctggtgg cttagtctct gagcgctcgc aggggtctgg gttaattgag     1800
actgtggtct ccctatgggg ttggcatccc catcagtttc ttcagtcctt ctcctattct     1860
tccatagagg tctctgactt cggtccaatg cttgactgta agtatctgca tctgtctcag     1920
tcagctgctg gtagagcctc tcagaggaca gccatgttag gctcctgact gcaagcacaa     1980
catgacatca gtaatagtgt tacgattgg tgcctgccca taggacatat cccttgcaga     2040
ccctaagaga tccaatgact gttttttaaat gaggctttag gcaagaggag ctttacttga    2100
```

<210> SEQ ID NO 4
<211> LENGTH: 303
<212> TYPE: DNA
<213> ORGANISM: mouse

<400> SEQUENCE: 4

```
ccatggggac atggctgtca tggtgtggaa gtgatagaaa tgaaacatg tatggatctg       60 tcacaggagc tggtgaggct gatgggtgtg tgggtggcca ctgtttgctc tctgcttgtc     120
acagcctctt gttcagggct tgatcaggga ggtgtgtgtg tgtgtgtgtg tgtgtgtgtg     180
tgtgtgtgtg tgtggtcaca cccatctcag cagatctgtc agctttcccg cttttgttag     240
agggtgatat catgcttcct ggggggagct ctggaagaca atgagcagcc actttcctct     300
aga                                                                   303
```

<210> SEQ ID NO 5
<211> LENGTH: 1257
<212> TYPE: DNA
<213> ORGANISM: rabbit

<400> SEQUENCE: 5

```
-continued atgctgctcc ctgtgccgct gctgctcggc ctgctcggcc tggccgccgc cgagcccgtc    60
gtctacttca aggagcagtt tctggacgga gatgggtgga ccgagcgctg gatcgaatcc   120
aaacacaagt ccgattttgg caaattcgtc ctcagttcgg gcaagttcta cggcgatcag   180
gagaaagata aagggctgca gaccagccag gacgcccgct tctacgccct gtcggcccga   240
ttcgagccgt tcagcaacaa gggccagcca ctggtggtgc agttcaccgt gaaacacgag   300
cagaacattg actgcggggg cggctacgtg aagctgtttc cggccggcct ggaccagaag   360
gacatgcacg gggactctga gtacaacatc atgtttggtc ctgacatctg tggccccggc   420
accaagaagg ttcacgtcat cttcaactac aagggcaaga acgtgctgat caacaaggac   480
atccgttgca aggacgacga gttcacacac ctgtacacgc tgatcgtgcg gccggacaac   540
acgtatgagg tgaagattga caacagccag gtggagtcgg gctccctgga ggatgactgg   600
gacttcctac cccccaagaa gataaaggac ccagatgcct cgaagcctga agactgggac   660
gagcgggcca agatcgacga ccccacggac tccaagcccg aggactggga caagcccgag   720
cacatccccg acccggacgc gaagaagccc gaagactggg acgaagaaat ggacggagag   780
tgggagccgc cggtgattca gaaccccgag tacaaggtg agtggaagcc gcggcagatc   840
gacaaccccg attacaaagg cacctggatc cacccccgaaa tcgacaaccc cgagtactcg   900
cccgacgcta acatctatgc ctacgacagc tttgccgtgc tgggcttgga cctctggcag   960
gtcaagtcgg gcaccatctt cgacaacttc ctcatcacca acgatgaggc gtacgcagag  1020
gagtttggca acgagacgtg gggcgtcacc aagacggccg agaagcagat gaaagacaag  1080
caggacgagg agcagcggct gaaggaggag gaggaggaga agaagcggaa ggaggaggag  1140
gaggccgagg aggacgagga ggacaaggac gacaaggagg acgaggatga ggacgaggag  1200
gacaaggacg aggaggagga ggaggcggcc gccggccagg ccaaggacga gctgtag     1257
```